United States Patent
Farrugia et al.

(10) Patent No.: US 10,113,059 B2
(45) Date of Patent: Oct. 30, 2018

(54) ANTI-BACTERIAL METALLO IONOMER POLYMER NANOCOMPOSITE POWDERS AND METHODS OF MAKING THE SAME

(71) Applicant: XEROX CORPORATION, Norwalk, CT (US)

(72) Inventors: Valerie M. Farrugia, Oakville (CA); Barkev Keoshkerian, Thornhill (CA); Michelle N. Chretien, Mississauga (CA)

(73) Assignee: XEROX CORPORATION, Norwalk, CT (US)

( * ) Notice: Subject to any disclaimer, the term of this patent is extended or adjusted under 35 U.S.C. 154(b) by 315 days.

(21) Appl. No.: 15/203,675

(22) Filed: Jul. 6, 2016

(65) Prior Publication Data

US 2018/0009975 A1    Jan. 11, 2018

(51) Int. Cl.

| | |
|---|---|
| C08L 33/08 | (2006.01) |
| A01N 25/26 | (2006.01) |
| A01N 59/16 | (2006.01) |
| C08F 212/08 | (2006.01) |
| C08J 3/12 | (2006.01) |
| C08F 265/06 | (2006.01) |
| C08F 6/18 | (2006.01) |
| B33Y 70/00 | (2015.01) |

(52) U.S. Cl.
CPC .............. *C08L 33/08* (2013.01); *A01N 25/26* (2013.01); *A01N 59/16* (2013.01); *B33Y 70/00* (2014.12); *C08F 6/18* (2013.01); *C08F 212/08* (2013.01); *C08F 265/06* (2013.01); *C08J 3/126* (2013.01); *C08F 2800/20* (2013.01); *C08L 2205/025* (2013.01); *C08L 2207/53* (2013.01)

(58) Field of Classification Search
CPC ...... C08L 33/08; C08L 2207/53; B33Y 70/00; A01N 25/26; A01N 59/16; C08F 6/18; C08F 212/08; C08F 265/06; C08F 2800/20; C08J 3/126
USPC ....................................... 428/407
See application file for complete search history.

(56) References Cited

U.S. PATENT DOCUMENTS

| | | | |
|---|---|---|---|
| 4,247,508 | A | 1/1981 | Housholder |
| 4,863,538 | A | 9/1989 | Deckard |
| 5,017,753 | A | 5/1991 | Deckard |
| 5,111,998 | A | 5/1992 | Kanda et al. |
| 5,147,753 | A | 9/1992 | Hikake |
| 5,272,034 | A | 12/1993 | Kawano et al. |
| 5,393,630 | A | 2/1995 | Bayley et al. |
| 6,110,411 | A | 8/2000 | Clausen et al. |
| 2015/0079504 | A1* | 3/2015 | Farrugia ............ G03G 9/09392 430/18 |

FOREIGN PATENT DOCUMENTS

| | | |
|---|---|---|
| CA | 2846196 A1 | 2/2013 |
| EP | 2773197 A1 | 9/2014 |
| WO | 2013026961 A1 | 2/2013 |
| WO | 2014/075185 A1 | 5/2014 |
| WO | WO2014/075185 * | 3/2015 |

OTHER PUBLICATIONS

Humberto Palza: "Antimicrobial Polymers with Metal Nanoparticles" IJOMS, vol. 16, No. 1, Jan. 19, 2015, pp. 2099-2116.*
Extended European Search Report re: Xerox Patent Application No. 17177851.7 dated Oct. 12, 2017, seven pages.
Humberto Palza: "Antimicrobial Polymers with Metal Nanoparticles", International Journal of Molecular Sciences, vol. 16, No. 1, Jan. 19, 2015, pp. 2099-2116.
Lok et al., "Silver nanoparticles: partial oxidation and antibacterial activities", J Biol Inorg Chem, 12:527-534, 2007.
Guggenbichler et al., "A New Technology of Microdispersed Silver in Polyurethane Induces Antimicrobial Activity in Central Venous Catheters", Infec 27, Suppl 1:S16-23, 1999.
Klueh et al., "Efficacy of Silver-Coated Fabric to Prevent Bacterial Colonization and Subsequent Device-Based Biofilm Formation", J Biomed Mater Res 53:621-631, 2000.
Davies & Etris, "The development and functions of silver in water purification and disease control", Catal Today 26:107 114, 1997.
Mukherjee et al., "Potential Theranostics Application of Bio-Synthesized Silver Nanoparticles (4-in-1 System)", Theran 2014; 4(3):316-335.
Rai et al., "Silver nanoparticles as a new generation of antimicrobials", Biotech Adv, 27:76-83, 2009.
Humberto Palza, "Antimicrobial Polymers with Metal Nanoparticles", Int. J. Mol. Sci. 2016 16 2099-2116.
Stutman et al., "Mechanism of Core/Shell Emulsion Polymerization", Ind. Eng. Chem. Prod. Res. Dev. 1985-24 412-417.
Zhang et al., "Perspective: Ionomer Research and Applications", Macromol. React, Eng. (2014) 8, 81-99.
Schmid et al., "Polymer Powders for Selective Laser Sintering (SLS)". Inspire, Institute for Rapid Product Development, Gallen. Switzerland.
Ebadi-Dehaghani et al., Thermal Conductivity of NP-filled Polymers, Smart Nanoparticles Technology, 2012), 519-540.
J.H. Choi et al., "Thermal conductivity estimation of Inkjet-printed silver nanoparticle ink during continuous wave laser sintering", International Journal of Heat and Mass Transfer 85 (2015) 904-909.
Warrier and Teja, "Effect of particle size on the thermal conductivity of nanofluids containing metallic nanoparticles", Nanoscale Research Letters 2011, 6:247.
Tsekmes et al, "Thermal Conductivity of Polymeric Composites: A Review", ICDS (2013), Bologna, Italy, Jun. 30-Jul. 4, 2013.

* cited by examiner

*Primary Examiner* — Leszek B Kiliman
(74) *Attorney, Agent, or Firm* — Pillsbury Winthrop Shaw Pittman LLP

(57) ABSTRACT

A composite powder includes a core particle comprising a styrene/acrylate polymer resin, and a shell comprising a styrene/acrylate ionomer resin, wherein the styrene/acrylate ionomer resin comprises a metal ion acrylate monomer, and methods of making thereof. Various articles can be manufactured from such composite powders.

20 Claims, 3 Drawing Sheets

ANTI-BACTERIAL METALLO IONOMER POLYMER NANOCOMPOSITE POWDERS AND METHODS OF MAKING THE SAME

CROSS-REFERENCE TO RELATED APPLICATIONS

Reference is made to commonly owned and co-pending, U.S. patent application Ser. No. 15/203,648 (not yet assigned) entitled "ANTI-BACTERIAL METALLO IONOMER POLYMER NANOCOMPOSITE FILAMENTS AND METHODS OF MAKING THE SAME" to Valerie M. Farrugia et al., electronically filed on the same day herewith, the entire disclosures of which are incorporated herein by reference in its entirety.

BACKGROUND

The present disclosure relates to composite powders, particularly, powders of metallo ionomer polymer nanocomposites, wherein the composite nanoparticle comprising a core and a shell. The nanocomposites can be use in selective laser sintering (SLS) application.

The medical community's reliance on three dimensional 3D printing for various applications is rapidly increasing and covers areas such as tissue and organ fabrication, customizable devices such as prosthetics, mouth guards, orthotics, hearing aids and implants, and pharmaceutical exploration related to controlled drug delivery and personalized drug production. Many of these medical applications require composite material that can inhibit bacterial, microbial, viral or fungal growth. Other products for 3D printing such as kitchen tools, toys, education materials and countless household items also provide a favorable environment for bacteria growth, and therefore antibacterial composite materials are also desirable for use in connection with these products. Due to the layered construction of 3D printed material, the potential for bacterial growth can be very significant, especially since certain bacterial strains can actually thrive within the detailed structural make-up of these materials. Washing alone does not completely sterilize the surfaces and crevasses of these products.

Therefore, there exists a need for new materials with antibacterial properties for 3D printing. One of the 3D printing methods is selective laser sintering (SLS), which is a common additive manufacturing (3D printing) technique. A detailed description of SLS technology can be found in U.S. Pat. Nos. 4,247,508, 4,863,538, 5,017,753, and 6,110,411, each incorporated herein by reference. SLS printing typically employs powdered plastics/polymers as build materials for printing objects. Most SLS materials are composites of polyamide (nylon) with or without additives such as powdered glass, carbon fibers, aluminum powder, etc. The powder is sintered into shape by a laser in a layer-by-layer fashion to build the objects from "scratch". Laser sintering usually uses particles ranging from about 50 to about 300 microns, where the degree of detail is limited only by the precision of the laser and fineness of the powder. The detail and intricacy of the objects derived through the SLS process is remarkable but also creates potential scaffolds for bacterial or microbial build-up, especially in applications related to health care and the food industry.

SUMMARY

In some aspects, embodiments herein relate to composite powder comprising a core particle comprising a styrene/acrylate polymer resin and optionally a first metal ion acrylate monomer; and a shell comprising a styrene/acrylate ionomer resin, wherein the styrene/acrylate ionomer resin comprises a second metal ion acrylate monomer; wherein the total amount of metal presented in the composite powder ranges in a concentration of from about 0.5 ppm to about 50,000 ppm; and further wherein the composite powder has a particle size of from about 10 microns to about 300 microns.

In some aspects, embodiments herein relate to method of producing a composite powder, comprising polymerizing a first mixture comprising a first styrene/acrylate copolymer to form a core styrene/acrylate polymer resin in an organic-free solvent; heating the core styrene/acrylate polymer resin; adding a shell styrene/acrylate ionomer resin by polymerizing a second mixture comprising a second styrene/acrylate copolymer and initiator to the formed polymer core styrene/acrylate polymer resin to form a shell disposed about the core styrene/acrylate polymer resin, thereby forming an emulsion of composite particles, wherein the shell styrene/acrylate ionomer resin comprises a metal; aggregating the emulsion of composite particles to form aggregated particles; coalescing the aggregated particles to form coalesced particles; washing the coalesced particles, thereby forming the composite powder.

In some aspects, embodiments herein relate to an article comprising a composite powder comprising a core particle comprising a styrene/acrylate polymer resin and optionally a first metal ion acrylate monomer; and a shell comprising a styrene/acrylate ionomer resin, wherein the styrene/acrylate ionomer resin comprises a second metal ion acrylate monomer; wherein the total amount of metal presented in the composite powder ranges in a concentration of from about 0.5 ppm to about 50,000 ppm; and further wherein the composite powder has a particle size of from about 10 microns to about 300 microns.

BRIEF DESCRIPTION OF DRAWINGS

Various embodiments of the present disclosure will be described herein below with reference to the figures wherein.

DETAILED DESCRIPTION

Figure 1:
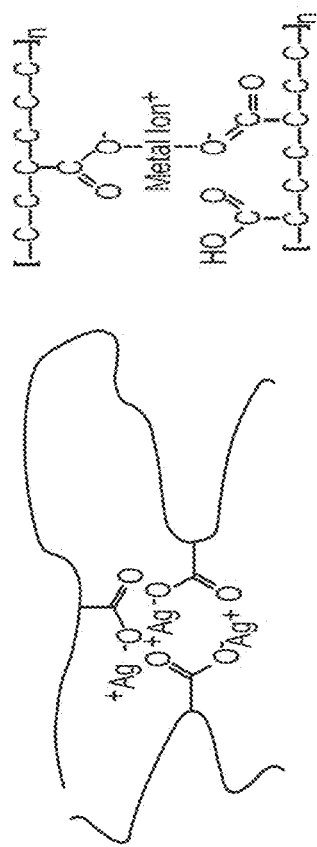
FIG. 1 shows schematic representations of ionic cross-links between ionomer-type polymers according to certain embodiments described herein.

As used herein, "a," "an," "the," "at least one," and "one or more" are used interchangeably. Thus, for example, a coating composition that comprises "an" additive can be interpreted to mean that the coating composition includes "one or more" additives.

Also herein, the recitations of numerical ranges includes disclosure of all subranges included within the broader range (e.g., 1 to 5 discloses 1 to 4, 1 to 3, 1 to 2, 2 to 4, 2 to 3, . . . etc.).

The term "ionomer," as used herein, refers to a polymer having covalent bonds between elements of the polymer chain and ionic bonds between the separate chains of the polymer. An ionomer is also known to be polymers containing inter-chain ionic bonding. An ionomer is a polymer that contains nonionic repeating units and a small portion of ionic repeating units which are usually pendant to a polymer backbone. Thus, an ionomer contains both ionic and covalent bonds. Covalent bonds exist along the polymer backbone chains. Ionic groups are attached to the backbone chain at random intervals. Depending on the ionomer morphology such as fraction and spacing of ionic functional groups, dielectric constant of the polymer matrix, chemical structure of the acid copolymer and local chemical conditions, such as pH, temperature, cation size or type (Zn, Ba, Cs, Cu, Na, Mg), dielectric matrix concentration, the ionic groups along the polymer backbone can form strong electrostatic interactions between other ionic groups which lead to nanoscale aggregation or physical crosslinks. These crosslinks enable significant improvement in the physical and chemical properties of ionomers compared to their non-ionic counterpart polymers.

The term, "metal acrylate(s)," such as, "silver acrylate(s)," as used herein, is collective for acrylate monomers comprising at least one metal atom, such as, a silver atom, for use in polymers, such as, silver acrylate and silver methacrylate which are monomers for a polymer comprising silver.

The term, "antibacterial," as used herein refers to the property of a composition for inhibiting or destroying the growth of bacteria. In other words, a toner particle comprising antibacterial properties is effective in killing bacteria, or in inhibiting growth or propagation of bacteria, including as a printed or fused image.

The term, "antimicrobial," as used herein refers to an agent, or the property imparted by the agent, that kills or inhibits growth of microorganisms or microbes. An antibacterial agent, or property thereof, is an antimicrobial agent. Microorganisms include, for example, bacteria, fungi, algae, other single celled organisms, protists, nematodes, parasites, other multicellular organisms, other pathogens and so on. In other words, a toner particle comprising antimicrobial properties is effective in killing microbes, or in inhibiting growth and propagation of microbes, including as a printed and fused image.

The term, "nano," as used in, "silver nanoparticles," indicates a particle size of less than about 1000 nm. In embodiments, the silver nanoparticles have a particle size of from about 0.5 nm to about 1000 nm, from about 1 nm to about 500 nm, from about 1 nm to about 100 nm, from about 1 nm to about 20 nm. The particle size is defined herein as the average diameter of the silver nanoparticles, as determined by TEM (transmission electron microscopy). In embodiments, the composite nanoparticle has a volume average particle diameter (D50) of from about 10 to about 600 nanometers, or from about 10 to about 300 nanometers, or from about 10 to about 200 nanometers.

The present disclosure provides a metallo ionomer polymer nanocomposite powder material for use in selective laser sintering (SLS) application.

The metallo ionomer polymer nanocomposites are metallo ionomer polymer latex (also refers to herein as "composite latex") that contain a core and a shell. In certain embodiments, the shell comprises an ionomer. In embodiments, the core comprises an ionomer. In embodiments, both the shell and the core each comprise an ionomer. In embodiments, the core comprising at least one styrene/acrylate polymer resin, optionally comprising a first metal ion acrylate monomer In embodiments, the shell comprising a styrene/acrylate ionomer resin (or styrene/acrylate metal ion polymer resin).

The metallo ionomer polymer nanocomposites may be prepared by emulsion polymerization. The emulsion polymerization technology may be used to incorporate a metal monomer into a polymer chain to provide added functionality to the metallo ionomer polymer latex. The metallo ionomer polymer latex may then be aggregated into micron-sized particles that are dried into a powder (hereinafter "composite powder") by a process similar to the emulsion aggregation (EA) for preparation of certain 2D (two-dimension) toner powders.

Core particles may be synthesized in an emulsion polymerization reaction, followed by polymerization of shell monomers on the surface of core particles.

In embodiments, the core resin comprises a silver composite monomer selected from the group consisting of a silver acrylate monomer, a silver methacrylate monomer, and combinations thereof.

The core resin may be synthesized using any of the styrene/acrylate copolymer disclosed herein or known in the art. Examples of styrene/acrylate copolymer include, but are not limited to, styrene acrylates, styrene butadienes, styrene methacrylates, and combinations thereof. In embodiments, are provided core resin particles wherein the polymers are selected from poly(styrene-alkyl acrylate), poly(styrene-1,3-diene), poly(styrene-alkyl methacrylate), poly(styrene-alkyl acrylate-acrylic acid), poly(styrene-1,3-diene-acrylic acid), poly(styrene-alkyl methacrylate-acrylic acid), poly(alkyl methacrylate-alkyl acrylate), poly(alkyl methacrylate-aryl acrylate), poly(aryl methacrylate-alkyl acrylate), poly(alkyl methacrylate-acrylic acid), poly(styrene-alkyl acrylate-acrylonitrile-acrylic acid), poly(styrene-1,3-diene-acrylonitrile-acrylic acid), poly(alkyl acrylate-acrylonitrile-acrylic acid), poly(styrene-butadiene), poly(methylstyrene-butadiene), poly(methyl methacrylate-butadiene), poly(ethyl methacrylate-butadiene), poly(propyl methacrylate-butadiene), poly(butyl methacrylate-butadiene), poly(methyl acrylate-butadiene), poly(ethyl acrylate-butadiene), poly(propyl acrylate-butadiene), poly(butyl acrylate-butadiene), poly(styrene-isoprene), poly(methylstyrene-isoprene), poly(methyl methacrylate-isoprene), poly(ethyl methacrylate-isoprene), poly(propyl methacrylate-isoprene), poly(butyl methacrylate-isoprene), poly(methyl acrylate-isoprene), poly(ethyl acrylate-isoprene), poly(propyl acrylate-isoprene), poly(butyl acrylate-isoprene), poly(styrene-propyl acrylate), poly(styrene-butyl acrylate), poly(styrene-butadiene-acrylic acid), poly(styrene-butadiene-methacrylic acid), poly(styrene-butadiene-acrylonitrile-acrylic acid), poly(styrene-butyl acrylate-acrylic acid), poly(styrene-butyl acrylate-methacrylic acid), poly(styrene-butyl acrylate-acrylonitrile), poly(styrene-butyl acrylate-acrylonitrile-acrylic acid), poly(styrene-butadiene), poly(styrene-isoprene), poly(styrene-butyl methacrylate), poly(styrene-butyl acrylate-acrylic acid), poly(styrene-butyl methacrylate-acrylic acid), poly(butyl methacrylate-butyl acrylate), poly(butyl methacrylate-acrylic acid), poly(acrylonitrile-butyl acrylate-acrylic acid) and combinations thereof.

A shell resin may be formed and then added to the core particle emulsion to form a layer encapsulating the core particles. A shell emulsion may be added to the reactor containing optionally heated core particle latex, which forms, "surface seeds," on core resin particles. Following formation of the core latex, an emulsion of shell monomers may be prepared and added to the emulsion of core particles wherein a shell comprising composite styrene/acrylate—metal ion polymer resin can be formed covering a part of or encapsulating, that is, covering the whole or entirety of the surface of core particles. In forming a shell emulsion, shell monomers, e.g., silver acrylate monomer, silver methacrylate monomer, and combinations thereof, optional chain transfer monomer, optional chain branching monomers may be added to an aqueous solution optionally comprising a surfactant. In certain embodiments, the silver monomer is present in the shell resin in an amount of from about 0.01 percent to about 10 percent, or from about 0.05 percent to about 8 percent, or from about 0.05 to about 4 percent, by weight based on the total weight of the shell reins. In embodiments, the shell comprises a styrene/acrylate ionomer resin, wherein the resin comprises a co-monomer selected from the group consisting of methyl methacrylate, butyl acrylate, diacrylate, cyclohexyl methacrylate, styrene, methacrylic acid, dimethylaminoethyl methacrylate or combinations thereof.

In embodiments, a shell resin is synthesized on core particles, wherein the appropriate shell monomers and an initiator are added to the core particles. In embodiments, a metal ion is reduced on a resin or on a core particle to form a shell thereover. In embodiments, metal can be reducing during formation of a core. In embodiments, a metal can be reduced on a core. In embodiments, metal can be reduced on a shell. A shell, such as, a resin comprising a metal or a reduce metal, for example, may cover the entire surface of a core particle or portions thereof. Hence, a shell can encompass the entire exterior surface of a particle, thereby encapsulating a core particle or be found, for example, at sites on the surface of a core, as isolated patches of varying size, islands and so on.

To complete polymerization of the shell resin, an aqueous solution of initiator, such as ammonium or potassium persulfate, may be slowly added to the reactor. Following addition of all reactants, the emulsion may be mixed and the heat maintained for an extended period of time, such as, about 6-24 hours. Following completion of the polymerization reaction, the emulsion can be cooled and the resin particles may be filtered or sieved, such as with a 25 μm screen.

In embodiments, a metal acrylate or metal methacrylate monomer may be incorporated in a styrene/acrylate polymer via polymerization, that is, as a monomer that is covalently bound to another monomer to form the polymer backbone. In embodiments, the present composite ionomer is prepared by emulsion polymerization in a reactor, wherein an emulsion of at least one silver acrylate monomer, a styrene/acrylate co-monomer, an optional branching agent and an optional chain transfer agent is added to a heated aqueous solution of surfactant. After reaching equilibrium, a solution of initiator can be added to the heated reactor and polymerization proceeds until completed. Formation of the latex comprising the composite ionomers may be done in isolation, wherein the ionomers optionally may be washed/screened/dried for future use, or a latex may be prepared as a multistep synthesis/polymerization of a further resin-based material, such as, a composite nanoparticle, or for production of articles.

Incorporation of silver monomers in an ionomer, such as, with emulsion polymerization, improves stabilization of the composite latex and also allows a controlled release of silver ions from the composite. In addition, the polymer backbone prevents the silver ions from aggregating since the silver ions essentially are bonded to and integrated in a polymer backbone and that enforces strict positioning of the silver ions along the polymer backbone for sensor or antimicrobial applications. The ionic polymer matrix provides a large active surface area of silver ions which can be spread strategically along the polymer backbone. For instance, the silver ions can be situated on the exterior shell of a core-shell nanoparticle for better exposure of metal ions to the environment.

Any metal ion acrylate monomer or methacrylate monomer useful for polymerization of a styrene/acrylate latex resin may be utilized. In embodiments, acrylic or methacrylic monomers may include, but are not limited to, acrylate, methacrylate and so on, wherein the metal ion acrylate monomers are reacted with a styrene/acrylate monomer, optionally a branching agent, optionally a chain transfer agent and optionally an initiator for synthesis of the present composite ionomer resin.

In embodiments, the optional core metal, if present, and the shell metal comprise a composite comprising silver and one or more other metals; wherein the optional core metal, if present, and the shell metal comprise a composite comprising silver and one or more non-metals; or wherein the optional core metal, if present, and the shell metal comprise a composite comprising silver, one or more other metals, and one or more non-metals.

Silver is known for antimicrobial properties, however, for silver to have any antimicrobial properties, generally, the silver must be ionized (Lok et al., J Biol Inorg Chem, 12:527-534, 2007; Rai et al., Biotech Adv, 27:76-83, 2009); non-ionized silver often is inert (Guggenbichler et al., Infec 27, Suppl 1:S16-23, 1999). It is thought silver atoms bind to thiol groups (—SH) in enzymes causing deactivation of the enzymes. Silver forms stable S—Ag bonds with thiol-containing compounds in the cell membrane that are involved in transmembrane energy generation and ion transport (Klueh et al., J Biomed Mater Res 53:621-631, 2000). It also is believed that silver can take part in catalytic oxidation reactions resulting in formation of disulfide bonds (R—S—S—R). Silver catalyzes reaction between oxygen molecules in the cell and hydrogen atoms of thiol groups: water is released as a product and two thiol groups become covalently bonded to one another through a disulfide bond (Davies & Etris, Catal Today 26:107-114, 1997). In addition, silver ions may interact with a cell destabilizing plasma membrane potential and reducing levels of intracellular adenosine triphosphate (ATP), resulting in cell death (Mukherjee et al., Theran 2014; 4(3):316-335). Silver is also known for electrical and thermal conductivity properties. The electrical and thermal conductivity of silver is the highest of all metals.

Those skilled in the art will appreciate that metals other than silver may be useful and can be prepared in accordance with the methods disclosed herein. Thus, for example, composites may be prepared with nanoparticles of copper, gold, palladium, or composites of such exemplary metals. See, for example, Adams C P, Walker K A, Obare S O, Docherty K M, PLoS One. 2014 Jan. 20; 9(1):e85981. doi: 10.1371/journal.pone.0085981, eCollection 2014, describing palladium as an antimicrobial.

In embodiments, the composite powders of the present disclosure further includes nanostructured materials, such as, without limitation, carbon nanotubes (CNTs, including single-walled, double-walled, and multi-walled), graphene sheet, nanoribbons, nano-anions, hollow nanoshell metals, nano-wires and the like. In embodiments, CNTs may be added in amounts that enhance electrical and thermal conductivity.

In embodiments are provided methods for preparing metallo ionomer polymer nanocomposite nanoparticles. Methods comprise forming core particles in an emulsion polymerization latex followed by polymerization of a shell resin on the surface of core particles, wherein a core can comprise a styrene/acrylate resin and a shell can comprise at least one composite styrene/acrylate—metal ion polymer resin. In embodiments, an emulsion of core monomers (styrene monomers, acrylate monomers, optional chain transfer agent, and optional branching agents) is added to a heated solution of aqueous surfactant followed by addition of an initiator. Core reactants are polymerized to form core styrene/acrylate particles, optionally comprising a metal. Shell resin may be polymerized on core particles by addition of shell monomers followed by addition of an initiator. Following addition of a shell layer partially covering or encapsulating core particles, composite nanoparticles optionally may be washed/screened/dried for future use, or a latex may be prepared as a multistep synthesis/polymerization of a further resin-based material, such as, for production of articles, such as, inks or toners. In embodiments, both core and shell comprise metal ion resins.

In embodiments are provided articles comprising powders of metallo ionomer polymer nanocomposites comprising at least one metal ion acrylate monomer. In embodiments are provided articles comprising powders of metallo ionomer polymer nanocomposites having a core and a shell, wherein the core comprises a styrene/acrylate resin, which can comprise a metal, and the shell comprises at least one composite styrene/acrylate—metal ion ionomer. An article may be selected from a biochemical sensor, an optical detector, an antimicrobial, a textile, a fuel cell, a functional smart coating, a solar cell, a cosmetic, an electronic component, a fiber, a cryogenic superconducting material and so on. In embodiments, composite nanoparticle and/or composite styrene/acrylate ionomer resin is used as a resin in inks (aqueous and dry), toner, antimicrobial coatings, additives, finishes, paint, composites for 3-dimensional printing and so on.

Table 1 illustrates two of the key monomers that can be selected for emulsion polymerization of metallo ionomer polymer latex are silver acrylate and silver acrylate.

TABLE 1

| Name | Molecular Weight |
| --- | --- |
| Silver Acrylate $\text{H}_2\text{C}=\underset{\text{H}}{\text{C}}-\overset{\text{O}}{\underset{\|}{\text{C}}}-\text{O}^- \; \text{Ag}^+$ | 192.95 |
| Silver Methacrylate $\text{H}_2\text{C}=\underset{\underset{\text{CH}_3}{\|}}{\text{C}}-\overset{\text{O}}{\underset{\|}{\text{C}}}-\text{O}^- \; \text{Ag}^+$ | 178.93 |

Semiconductive electrical properties of the present silver ionomers were analyzed wherein ζ potential was measured. As understood in the art, ζ potential is a measure of magnitude of electrostatic or charge repulsion/attraction between particles and is a fundamental parameter known to impact stability. In other words, ζ potential, also referred to as electrokinetic potential, is an indirect measure or indicator of stability of ionomer particle dispersion. For example, ζ potential measurement may bring detailed insight into causes of dispersion, aggregation or flocculation, and can be used to improve formulation of dispersions, emulsions and suspensions. ζ potential reflects a potential difference between dispersion medium and stationary layer of fluid attached to dispersed particles.

Magnitude of ζ potential indicates the degree of electrostatic repulsion between adjacent, similarly charged particles in a dispersion. For molecules and particles that are small enough, a high ζ potential relates to stability, generally, a value of at least about −55, at least about −65 or lower (greater absolute value) is desirable. The silver composite ionomer, containing silver acrylate, had a measured ζ potential of −65.5 mV, which indicates stability of the composite ionomer particle dispersion.

The interaction between ionic silver and carboxylate groups, which act as ionic crosslinks, may have an effect on the properties of the polymer matrix, such as, solubility in chemical solvents, glass transition temperature, molecular weight, and water sensitivity. Representations of ionic crosslinks between ionomer type polymers according to certain embodiments of the disclosure are shown in FIG. 1.

Composite Powder Synthesized from the Metallo Ionomer Polymer Nanocomposite

Composite powders as described herein are first prepared from the metallo ionomer polymer nanocomposite. Composite powders may be prepared by conventional (ground and classification) or chemical (emulsion aggregation) means. U.S. Pat. Nos. 5,111,998, 5,147,753, 5,272,034, and 5,393,630 disclose conventional toner manufacturing processes are incorporated in their entirety by reference herein.

Composite powders may be prepared by emulsion aggregation means. Any suitable emulsion aggregation procedure may be used in forming the emulsion aggregation composite particles without restriction. The method to prepare composite powders from the metallo ionomer polymer latex is similar to the process known to generate toner particles (emulsion aggregation or EA). Particles of narrow size distribution and controllable particle size can be achieved with the aid of aggregating agents such as zinc acetate, magnesium chloride salts, aluminum sulfate and polyaluminum chloride (PAC). The particle morphology can be controlled via temperature, time, and stirring to provide particles that range from an irregularly shaped or an imperfect spherical to a near or perfect spherical.

Figure 3:
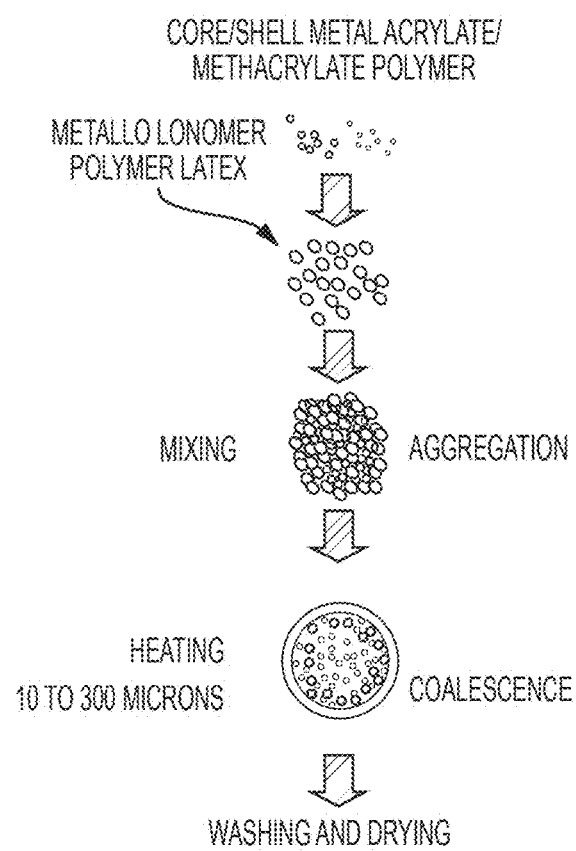
FIG. 3 shows a schematic of a possible mechanism of the preparation of dry particles for selective laser sintering (SLS) process.

FIG. 3 shows an emulsion aggregation process for preparing dry particles for Selective Laser Sintering (SLS) according to certain embodiments of the present disclosure. These procedures typically include the process steps of aggregating an emulsion of particles, such as those described in the present disclosure, a metallo ionomer polymer latex, and one or more additional optional additives to form aggregated particles, subsequently coalescing the aggregated particles, and then recovering, optionally washing and optionally drying the obtained emulsion aggregation particles. However, in embodiments, the process can be modified by the addition of a coalescent agent (or coalescence aid agent) prior to the coalescence. This addition of the coalescent agent provides toner particles having improved spheroidization, and allows the coalescence to be conducted in a shorter time, at a lower process temperature, or both. The aggregating step includes heating the slurry to a temperature of from about 30° C. to about 80° C., from about 40° C. to about 70° C., or from about 50° C. to about 68° C. The duration of the aggregation step may be from about 1 minute to about 8 hours, from about 30 minutes to about 6 hour, or from about 60 minutes to about 4 hours. The coalescing step includes heating the aggregated particles to a temperature of from about 30° C. to about 95° C., from about 40° C. to about 95° C., or from about 60° C. to about 90° C. The duration of the coalescing step may be from about 1 minute to about 6 hours, from about 30 minutes to about 4 hour, or from about 60 minutes to about 3 hours.

Examples of suitable coalescent agents include, but are not limited to, benzoic acid alkyl esters, ester-alcohols, glycol-ether type solvents, long-chain aliphatic alcohols, aromatic alcohols, mixtures thereof, and the like. Examples of benzoic acid alkyl esters include benzoic acid alkyl esters where the alkyl group, which can be straight or branched, substituted or unsubstituted, has from about 2 to about 30 carbon atoms, such as decyl or isodecyl benzoate, nonyl or isononyl benzoate, octyl or isooctyl benzoate, 2-ethylhexyl benzoate, tridecyl or isotridecyl benzoate, 3,7-dimethyloctyl benzoate, 3,5,5-trimethylhexyl benzoate, mixtures thereof, and the like. Specific commercial examples of such benzoic acid alkyl esters include VELTA® 262 (isodecyl benzoate) and VELTA® 368 (2-ethylhexyl benzoate), available from Vlesicol Chemical Corporation. Examples of ester-alcohols include hydroxyalkyl esters of alkanoic acids where the alkyls group, which can be straight or branched, substituted or unsubstituted, independently have from about 2 to about 30 carbon atoms, such as 2,2,4-trimethylpentane-1,3-diol monoisobutyrate. Specific commercial examples of such ester-alcohols include TEXANOL® (2,2,4-trimethylpentane-1,3-diol monoisobutyrate) available from Eastman Chemical Company. Examples of glycol-ether type solvents include diethylene glycol monomethylether acetate, diethylene glycol monobutylether acetate, butyl carbitol acetate (BOA), and the like. Examples of long-chain aliphatic alcohols include those where the alkyl group is from about 5 to about 20 carbon atoms, such as ethylhexanol, octanol, dodecanol, and the like. Examples of aromatic alcohols include benzyl alcohol, and the like.

In embodiments, the coalescent agent (or coalescence aid agent) evaporates during later stages of the emulsion aggregation process or during coalescence, such as during the heating step that is generally near or above the glass transition temperature of the sulfonated polyester resin. The final composite powders are thus free of, or essentially or substantially free of, any remaining coalescent agent. To the extent that any remaining coalescent agent may be present in the final powder composites, the amount of remaining coalescent agent is such that it does not affect any properties or performance of the composite powders.

The coalescent agent can be added prior to the coalescence (or right at the beginning prior to heating or aggregation) in any desired or suitable amount. For example, the coalescent agent can be added in an amount of from about 0.01 to about 10 percent by weight, based on the solids content in the reaction medium. For example, the coalescent agent can be added in an amount of from about 0.05 or from about 0.1 to about 0.5 or to about 5.0 percent by weight, based on the solids content in the reaction medium. In embodiments, the coalescent agent can be added at any time between aggregation and coalescence, or upfront before heating.

Optional additives such as waxes, pigments, ceramics, carbon fiber or nanotubes, and fillers may be included in the composite powder. These additives may be added prior to or during the aggregation step or upfront before heating. The amount of additives present in the composite powder may be from about 0% to about 30%, from about 0% to about 20%, or from about 0% to about 10% by weight of the total weight of the composite powder.

The method of preparing the composite powder of the present disclosure comprising polymerizing a first mixture comprising a first styrene/acrylate copolymer to form a core styrene/acrylate polymer resin ("seed") in an organic free solvent, heating the core styrene/acrylate polymer resin; adding a shell styrene/acrylate ionomer resin by polymerizing a second mixture comprising a second styrene/acrylate copolymer and initiator to the formed core styrene/acrylate polymer resin to form a shell disposed about the core particles, thereby forming an emulsion of composite particles, wherein the shell styrene/acrylate ionomer resin comprises a metal; aggregating the emulsion of composite particles to form aggregated particles; coalescing the aggregated particles to form coalesced particles; washing the coalesced particles, thereby forming the composite powder; thereby forming the composite powder. In embodiments, the polymerizing step to form a core styrene/acrylate polymer resin in an organic-free solvent and the emulsifying step including heating the core styrene/acrylate polymer resin occur simultaneously. In embodiments, the polymerizing step is performed in an aqueous media. The core styrene/acrylate polymer resin is an emulsion.

The term "organic-free solvent" refers to media that does not contain any organic solvent An aqueous media such as water is considered to be an organic-free solvent.

In embodiments, heating is conducted at a temperature from about 65° C. to about 90° C. Temperatures in this range are appropriate for both the initial dissolution of the polymer resin and subsequent reduction in the presence of silver ion.

In embodiments, methods disclosed herein may be particularly well-suited for making composites with relatively low solids content. Under such conditions, silver ion and reducing agent may readily diffuse through the polymer matrix. In the case of silver ion, such ready diffusion may improve uniformity of distribution of silver throughout the matrix.

In embodiments, a loading of metal and/or metal ion (in the form of a metal ion methacrylate or acrylate) is present in the composite powder in a range from about 0.5 ppm to about 50,000 ppm, from about 5 ppm to about 5,000, from about 10 ppm to about 2,500, ppm, or from about 50 ppm to about 1,000 ppm. Loading concentrations of metal/metal ion within this range can be used for antibacterial applications.

The final composite powders can be of any desired size, in embodiments, the composite powders may have a particle size of from about 10 microns to about 300 microns, from about 10 microns to about 100 microns, or from about 5 microns to about 20 microns. The use of composite powders in the smaller particle size range (e.g., 5-20 microns) may be advantageous in SLS relative to the typical particle size ranges (100-300 microns) due to the fine-grained nature of the shapes thus available. In embodiments, the composite powders have a particle size distribution with a lower number ratio geometric standard deviation (GSD) of from about 1.0 to about 4.0, from about 1.1 to about 3.0, or from about 1.2 to about 2.0. The final composite powders can be of any desired shape, either coarse or spherical. Spherical particles are generally desired for optimal packing and fusing/welding.

The composite powder may have a glass transition temperature (Tg) of from about −50° C. to about 400° C., from about 50° C. to about 300° C. or from about 80° C. to about 200° C. The composite powder may have a thermal conductivity of from about 0.04 W/(mK) to about 50 W/(mK). The composite powder may have a weight average molecular weight of from about 10,000 to about 600,000, from about 20,000 to about 300,000, or from about 40,000 to about 200,000.

It is well known in the art that all polymer melt viscosities for a given polymer increase with the molecular weight of the polymer. Thus, lowering the molecular weight of a given polymer decreases its melt viscosity and consequently enhances its flow characteristics. However, it is also well known in the art that for a given polymer, mechanical properties decrease with decreasing molecular weight. The composite powder of the present disclosure optimizes flow characteristics and mechanical properties, in part, by not sacrificing molecular weight to obtain acceptable flow characteristics. The composite powder may have a melt flow index (MFI) of from about 0.2 grams/10 minutes to about 50 grams/10 minutes, from about 2 grams/10 minutes to about 40 grams/10 minutes, or from about 5 grams/10 minutes to about 30 grams/10 minutes as measured at 200° C. with a 2.16 kilogram weight which is the typical load for thermoplastic resins.

The properties of the composite powder herein make them useful in various applications including, without limitation, electronics components, optical detectors, chemical and biochemical sensors and devices. The ability to miniaturize any of these materials is a major benefit of using the nanoscale composite structures herein. Other areas of interest that employ the composite powder herein include, without limitation, antibacterial applications, optical bi-stability, textiles photoresponsivity, environmental, biological, medicine (membranes and separation devices), functional smart coatings, fuel and solar cells, and as catalysts.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

Example 1

This example describes the preparation of an Emulsion Polymerization Latex with 1% Silver Methacrylate A latex emulsion comprised of polymer particles generated from emulsion polymerization of styrene, n-butyl acrylate and silver methacrylate was prepared as follows.

A surfactant solution of 0.69 g Dowfax 2A1 (anionic surfactant, Dow) and 83.4 g de-ionized water (DIW) was prepared by mixing for 10 min in a 500 ml round bottom flask that was placed on an electric heating mantle and purged with nitrogen. The flask was purged continuously with nitrogen while being stirred at 195 rpm. The reactor was heated to 70° C. at a controlled rate. Separately, 1.52 g of ammonium persulfate (APS) initiator was dissolved in 13.3 g of DIW. Separately, 73.54 g of styrene, 27.58 g of butyl acrylate, 1.02 g of silver methacrylate, 1.78 g of 1-dodecanethiol (DDT) and 0.36 g of 1,10-decanediol diacrylate (ADOD) were added to a premix of 3.91 g of Dowfax 2A1 in 44.68 g of DIW and mixed to form an emulsion. Then, 7.44% of the above emulsion (7.63 g) was dropped slowly into the reactor containing the aqueous surfactant phase at 70° C. to form, "seeds," while being purged with nitrogen. The initiator solution was charged slowly into the reactor. The monomer emulsion feed then was started and added over 140 min. Once all the monomer emulsion was charged into the reactor flask, the stirring was increased to 210 rpm and the temperature was held at 70° C. overnight (approximately 20 hrs) to complete the reaction. The heat was turned off and the latex was left to cool while stirring. The product then was sieved through a 25 μm screen.

Figure 2:
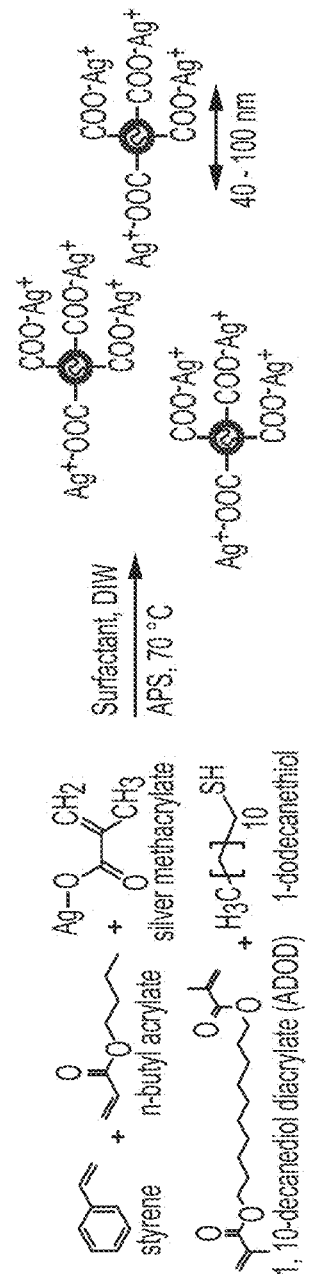
FIG. 2 shows a schematic of mechanism of bulk emulsion polymerization of latex particles containing Ag-based monomer according to certain embodiments described herein.

A schematic of mechanism of bulk emulsion polymerization of latex particles containing silver-based monomer is shown in FIG. 2.

Table 1 summarizes the content and quantity of the ingredients used in the emulsion polymerization.

TABLE 1

|  | grams | % relative to total | % rel. to total monomer |
|---|---|---|---|
| Styrene | 73.54 | 28.35% | 71.75% |
| nButyl Acrylate | 27.58 | 10.63% | 26.91% |
| Silver Methacrylate | 1.02 | 0.39% | 1.00% |
| 1,10-decanediol diacrylate | 0.36 | 0.14% | 0.35% |
| Dowfax 2A1 (aqueous) | 0.69 | 0.27% | 0.67% |
| Dowfax 2A1 (monomer) | 3.91 | 1.51% | 3.81% |
| n-dodecanethiol (DDT) | 1.78 | 0.69% | 1.74% |
| Water (aqueous phase) | 83.40 | 32.15% |  |
| Water (monomer phase) | 44.68 | 17.22% |  |
| Seed (from initial) | 7.63 | 2.94% | 7.44% |
| APS | 1.52 | 0.59% | 1.48% |
| Water (in initiator solution) | 13.30 | 5.13% |  |
| Total (grams) | 259.41 |  | 102.50 |

The particle size was measured by NANOTRAC U2275E particle size analyzer and found to have a D50 of 83.2 nm and D95 of 127.6 nm. The solids content was 35.15%.

Examples 2 and 3

These two examples describe the preparation of styrene/N-butyl acrylate core silver/methyl methacrylate shell latexes using sodium dodecyl sulfate (SDS).

For the initial solution for both examples, sodium dodecyl sulfate (SDS) was dissolved in dH2O in a three-necked round-bottom flask equipped with a reflux condenser, overhead stirrer and nitrogen exit and heated to 70° C. (200 RPM). The core monomer mixture was prepared by adding styrene, n-butyl acrylate and dodecanethiol (DDT) to a beaker. SLS was dissolved in deionized water (dH$_2$O) and added to the core monomer mixture. The monomer was emulsified with rapid mechanical stirring for 5 minutes followed by rest for 5 minutes, and repeated twice for a total of three times. 7.71 g of the core monomer mixture from Example 2 and 4.61 g of the core monomer mixture from Example 3, as shown in Table 2, were added to their respective reactors as a seed. The initiator for both examples were prepared by dissolving 1.38 g potassium persulfate (KPS) and 0.74 g sodium bicarbonate in 13.0 g dH$_2$O and added to the respective reactors dropwise. The remaining core monomer emulsion was fed into the reactor by pump at a rate of 0.7 g/min. The shell monomer mixture was prepared by dissolving Ag methacrylate in methyl methacrylate and adding DDT. SDS was dissolved in dH$_2$O and added to the shell monomer mixture. The shell monomer was emulsified with rapid mechanical stirring for 5 minutes followed by rest for 5 minutes, repeated twice for a total of three times. 2.17 g of the shell monomer mixture from Example 2 and 1.00 g of the shell monomer mixture from Example 3 was added to the respective reactors as a seed. The initiator for both Example 2 and 3 were prepared by dissolving 0.35 g KPS and 0.184 g sodium bicarbonate in 3.3 g dH$_2$O and added to the respective reactor dropwise. The remaining shell monomer emulsion was added to the respective reactor dropwise (240 RPM). The reaction was allowed to proceed at 70° C. overnight (200 RPM) before the latex was cooled to room temperature and sieved through a 25 μm sieve. The final appearance of both latexes was a dark grey opaque emulsion.

Table 2 summaries the content and quantities of the reactants.

TABLE 2

| Component | | Example 2 (in grams) | Example 3 (in grams) |
|---|---|---|---|
| Initial Solution | SLS | 2.520 | 1.89 |
| | $dH_2O$ | 81.20 | 85.5 |
| Core Monomer | styrene | 41.00 | 71.75 |
| | N-butyl acrylate | 51.25 | 20.50 |
| | DDT | 2.38 | 2.38 |
| | $dH_2O$ | 43.53 | 44.19 |
| | SLS | 5.87 | 4.40 |
| Seed amount removed from Core Monomer Emulsion | Core Seed | 7.71 | 4.61 |
| Initiator Mixture for Core Seed | KPS | 1.38 | 1.38 |
| | $NaHCO_3$ | 0.74 | 0.74 |
| | $dH_2O$ | 13.0 | 13.0 |
| Shell Monomer | Ag Methacrylate | 1.00 | 1.00 |
| | Methyl methacrylate | 9.23 | 9.23 |
| | DDT | 0.42 | 0.42 |
| | $dH_2O$ | 10.0 | 10.0 |
| | SLS | 1.0 | 1.0 |
| Seed amount removed from Shell Monomer Emulsion | Shell Seed | 2.17 | 1.00 |
| Initiator Mixture for Shell Seed | KPS | 0.35 | 0.35 |
| | $NaHCO_3$ | 0.184 | 0.184 |
| | $dH_2O$ | 3.30 | 3.30 |

The results in Table 3 provides the analytical data of the three latexes synthesized with silver methacrylate in Examples 1-3. As shown, the latex of Example 1 demonstrates a very large molecular weight as compared to that of Examples 2 and 3. Chain entanglements of the polymer may be due to the ionic interactions that contribute to physical cross-links in the polymer chains. This phenomenon is seen in the bulk EP process versus the core/shell EP process due to the positioning of the ionomer throughout the whole polymer in the bulk formulation in Example 1 as opposed to being selectively added to the shell only as in Example 2 and 3.

TABLE 3

| Measurement | Example 1 | Example 2 | Example 3 |
|---|---|---|---|
| Solids Content (%) | 35.15 | 29.49 | 22.01 |
| D50 Particle Size (Nanometers) | 83.2 | 42.1 | 43.9 |
| Zeta potential (mV) | −64.5 | −82.4 | −63.6 |
| Zeta deviation (mV) | 12.5 | 10.5 | 12.8 |
| Silver content by ICP (ppm) | 33.8 | 204.2 | 310.2 |
| Tg (onset) | 51.84° C. | 93.47° C. | 43.26° C. |
| Molecular Weight | 189,304 | 20,378 | 14,989 |

Example 4

This example shows the preparation of a composite powder.

In a 2 L glass reactor, a latex emulsion containing 200 g of silver acrylate-based copolymer obtained from Example 1 and 200 g of deionized water is premixed to give total solids of 17.6%, the pH is adjusted from about 2.0 to 3.0 with 1 M NaOH. The slurry is then homogenized using an IKA ULTRA TURRAX T50 homogenizer operating at about 3,000-4,000 RPM. During homogenization about 28 g of a flocculent mixture containing about 2.8 g polyaluminum chloride mixture and about 25.2 g 0.02 M nitric acid solution is added to the slurry. Thereafter, the 2 L glass reactor is transferred to a heating mantle; the RPM is set to 230 and heated to a temperature of about 50° C. where samples are taken to determine the average particle size. Once the particle size of the slurry is about 15 microns as measured with a Coulter Counter is achieved, freezing begins with the pH of the slurry being adjusted to about 4.5-5.0 using a 4% NaOH solution while also decreasing the reactor RPM to 75. The reactor temperature is ramped to 96° C. Once at the coalescence temperature, the slurry is coalesced for about 3 hours until the particle circularity is between 0.975-0.980 as measured by the Flow Particle Image Analysis (FPIA) instrument. The slurry is then cooled. The final particle size of the slurry is about 15.5 microns, GSDv 1.25, GSDn 1.25 and a circularity of 0.981. The slurry is then discharged from the reactor and the particles are filtered from the mother liquor and washed 2 times with deionized water (DIW). The final slurry is re-dispersed into 200 mL of deionized water, frozen via shell-freezer, and placed on drier for 3 days to result in dry particles to be used for SLS additive manufacturing in Example 5.

Example 5

This example demonstrates the antibacterial activities of aqueous-based latexes according to embodiments of the present disclosure.

Figure 4:
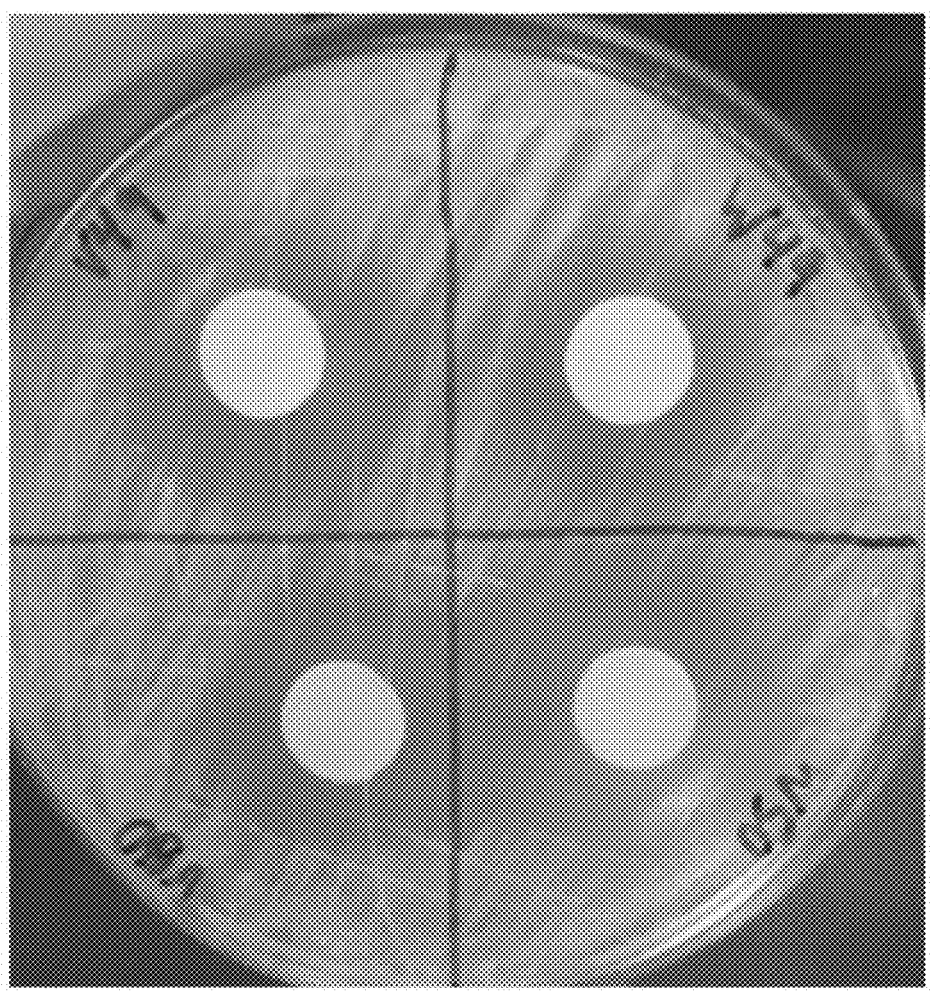
FIG. 4 shows a photo image of a petri dish containing silver methacrylate latex-suspensions synthesized from Example 2 (top half) and Example 3 (bottom half) being placed on two different substrates after incubation.

To test antibacterial properties suspensions made from latexes of Examples 2 and 3 were dip-coated onto different substrates (VWR410 qualitative filter paper and Whatman 6 qualitative filter paper). The solvent was evaporated and the substrate was placed onto an inoculated petri dish containing general purpose powdered medium for the cultivation of less fastidious microorganisms (nutrient agar; N0394 FLUKA). The dish was incubated overnight at 37° C. After 24 hours, large zones of inhibition were observed for both suspensions made from latex in Example 2 (top half) and Example 3 (bottom half) on the two substrates: VWR410 qualitative filter paper (left) and Whatman 6 qualitative filter paper (right). (FIG. 4).

What is claimed is:

1. A composite powder comprising:
   a core particle comprising a styrene/acrylate polymer resin and optionally a first metal ion acrylate monomer; and
   a shell comprising a styrene/acrylate ionomer resin, wherein the styrene/acrylate ionomer resin comprises a second metal ion acrylate monomer;
   wherein the total amount of metal presented in the composite powder ranges in a concentration of from about 0.5 ppm to about 50,000 ppm; and further wherein the composite powder has a particle size of from about 10 microns to about 300 microns.

2. The composite powder of claim 1, wherein the first metal of the shell comprises a silver.

3. The composite powder of claim 1, wherein the styrene/acrylate ionomer resin of the shell comprises a silver monomer selected from a silver acrylate monomer, a silver methacrylate monomer or combinations thereof.

4. The composite powder of claim 3, wherein the silver monomer is present in the shell resin from about 0.01% to about 10% by weight of the total monomers.

5. The composite powder of claim 1, wherein the styrene/acrylate ionomer resin of the shell comprises a co-monomer selected from methyl methacrylate, butyl acrylate, diacrylate, cyclohexyl methacrylate, styrene, methacrylic acid, dimethylaminoethyl methacrylate or combinations thereof.

6. The composite powder of claim 1, wherein the styrene/acrylate polymer resin of the core is selected from the group consisting of styrene acrylates, styrene butadienes, styrene methacrylates, and combinations thereof.

7. The composite powder of claim 6, wherein the styrene/acrylate polymer resin of the core is selected from the group consisting of poly(styrene-alkyl acrylate), poly(styrene-1,3-diene), poly(styrene-alkyl methacrylate), poly(styrene-alkyl acrylate-acrylic acid), poly(styrene-1,3-diene-acrylic acid), poly(styrene-alkyl methacrylate-acrylic acid), poly(alkyl methacrylate-alkyl acrylate), poly(alkyl methacrylate-aryl acrylate), poly(aryl methacrylate-alkyl acrylate), poly(alkyl methacrylate-acrylic acid), poly(styrene-alkyl acrylate-acrylonitrile-acrylic acid), poly(styrene-1,3-diene-acrylonitrile-acrylic acid), poly(alkyl acrylate-acrylonitrile-acrylic acid), poly(styrene-butadiene), poly(methylstyrene-butadiene), poly(methyl methacrylate-butadiene), poly(ethyl methacrylate-butadiene), poly(propyl methacrylate-butadiene), poly(butyl methacrylate-butadiene), poly(methyl acrylate-butadiene), poly(ethyl acrylate-butadiene), poly(propyl acrylate-butadiene), poly(butyl acrylate-butadiene), poly(styrene-isoprene), poly(methylstyrene-isoprene), poly(methyl methacrylate-isoprene), poly(ethyl methacrylate-isoprene), poly(propyl methacrylate-isoprene), poly(butyl methacrylate-isoprene), poly(methyl acrylate-isoprene), poly(ethyl acrylate-isoprene), poly(propyl acrylate-isoprene), poly(butyl acrylate-isoprene), poly(styrene-propyl acrylate), poly(styrene-butyl acrylate), poly(styrene-butadiene-acrylic acid), polystyrene-butadiene-methacrylic acid), poly(styrene-butadiene-acrylonitrile-acrylic acid), poly(styrene-butyl acrylate-acrylic acid), poly(styrene-butyl acrylate-methacrylic acid), poly(styrene-butyl acrylate-acrylonitrile), poly(styrene-butyl acrylate-acrylonitrile-acrylic acid), poly(styrene-butadiene), poly(styrene-isoprene), poly(styrene-butyl methacrylate), poly(styrene-butyl acrylate-acrylic acid), poly(styrene-butyl methacrylate-acrylic acid), poly(butyl methacrylate-butyl acrylate), poly(butyl methacrylate-acrylic acid), poly(acrylonitrile-butyl acrylate-acrylic acid) and combinations thereof.

8. The composite powder of claim 1 having a glass transition temperature (Tg) of from about −50° C. to about 400° C.

9. The composite powder of claim 1 having a thermal conductivity of from about 0.04 W/(mK) to about 50 W/(mK).

10. The composite powder of claim 1 having a weight average molecular weight of from about 10,000 to about 600,000.

11. The composite powder of claim 1 further comprises an additive selected from the group consisting of a wax, a pigment, a ceramic, a carbon fiber, a nanotube, or a combination thereof.

12. A method of producing a composite powder, comprising:
polymerizing a first mixture comprising a first styrene/acrylate copolymer to form a core styrene/acrylate polymer resin in an organic-free solvent;
heating the core styrene/acrylate polymer resin;
adding a shell styrene/acrylate ionomer resin by polymerizing a second mixture comprising a second styrene/acrylate copolymer and initiator to the formed polymer core styrene/acrylate polymer resin to form a shell disposed about the core styrene/acrylate polymer resin, thereby forming an emulsion of composite particles, wherein the shell styrene/acrylate ionomer resin comprises a metal;
aggregating the emulsion of composite particles to form aggregated particles; coalescing the aggregated particles to form coalesced particles;
washing the coalesced particles, thereby forming the composite powder.

13. The method of claim 12, wherein the metal is silver, copper, gold, palladium, or mixtures thereof.

14. The method of claim 12, wherein the styrene/acrylate ionomer resin of the shell comprises a silver monomer selected from a silver acrylate monomer, a silver methacrylate monomer or combinations thereof.

15. The method of claim 12, wherein the core comprising a styrene/acrylate polymer resin selected from the group consisting of poly(styrene-alkyl acrylate), poly(styrene-1,3-diene), poly(styrene-alkyl methacrylate), poly(styrene-alkyl acrylate-acrylic acid), poly(styrene-1,3-diene-acrylic acid), poly(styrene-alkyl methacrylate-acrylic acid), poly(alkyl methacrylate-alkyl acrylate), poly(alkyl methacrylate-aryl acrylate), poly(aryl methacrylate-alkyl acrylate), poly(alkyl methacrylate-acrylic acid), poly(styrene-alkyl acrylate-acrylonitrile-acrylic acid), poly(styrene-1,3-diene-acrylonitrile-acrylic acid), poly(alkyl acrylate-acrylonitrile-acrylic acid), poly(styrene-butadiene), poly(methylstyrene-butadiene), poly(methyl methacrylate-butadiene), poly(ethyl methacrylate-butadiene), poly(propyl methacrylate-butadiene), poly(butyl methacrylate-butadiene), poly(methyl acrylate-butadiene), poly(ethyl acrylate-butadiene), poly(propyl acrylate-butadiene), poly(butyl acrylate-butadiene), poly(styrene-isoprene), poly(methylstyrene-isoprene), poly(methyl methacrylate-isoprene), poly(ethyl methacrylate-isoprene), poly(propyl methacrylate-isoprene), poly(butyl methacrylate-isoprene), poly(methyl acrylate-isoprene), poly(ethyl acrylate-isoprene), poly(propyl acrylate-isoprene), poly(butyl acrylate-isoprene), poly(styrene-propyl acrylate), poly(styrene-butyl acrylate), poly(styrene-butadiene-acrylic acid), poly(styrene-butadiene-methacrylic acid), poly(styrene-butadiene-acrylonitrile-acrylic acid), poly(styrene-butyl acrylate-acrylic acid), poly(styrene-butyl acrylate-methacrylic acid), poly(styrene-butyl acrylate-acrylonitrile), poly(styrene-butyl acrylate-acrylonitrile-acrylic acid), poly(styrene-butadiene), poly(styrene-isoprene), poly(styrene-butyl methacrylate), poly(styrene-butyl acrylate-acrylic acid), poly(styrene-butyl methacrylate-acrylic acid), poly(butyl methacrylate-butyl acrylate), poly(butyl methacrylate-acrylic acid), poly(acrylonitrile-butyl acrylate-acrylic acid) and combinations thereof.

16. The method of claim 12, wherein the aggregating is conducted at a temperature of from about 30° C. to about 80° C.

17. The method of claim 12, wherein the coalescing is conducted at a temperature of from about 30° C. to about 95° C.

18. An article comprising:
a composite powder comprising:
a core particle comprising a styrene/acrylate polymer resin and optionally a first metal ion acrylate monomer; and a shell comprising a styrene/acrylate ionomer resin, wherein the styrene/acrylate ionomer resin comprises a second metal ion acrylate monomer;

wherein the total amount of metal presented in the composite powder ranges in a concentration of from about 0.5 ppm to about 50,000 ppm; and further wherein the composite powder has a particle size of from about 10 microns to about 300 microns.

19. The article of claim 18, wherein, wherein the styrene/acrylate polymer resin of the core is selected from the group consisting of poly(styrene-alkyl acrylate), poly(styrene-1,3-diene), poly(styrene-alkyl methacrylate), poly(styrene-alkyl acrylate-acrylic acid), poly(styrene-1,3-diene-acrylic acid), poly(styrene-alkyl methacrylate-acrylic acid), poly(alkyl methacrylate-alkyl acrylate), poly(alkyl methacrylate-aryl acrylate), poly(aryl methacrylate-alkyl acrylate), poly(alkyl methacrylate-acrylic acid), poly(styrene-alkyl acrylate-acrylonitrile-acrylic acid), poly(styrene-1,3-diene-acrylonitrile-acrylic acid), poly(alkyl acrylate-acrylonitrile-acrylic acid), poly(styrene-butadiene), poly(methylstyrene-butadiene), poly(methyl methacrylate-butadiene), poly(ethyl methacrylate-butadiene), poly(propyl methacrylate-butadiene), poly(butyl methacrylate-butadiene), poly(methyl acrylate-butadiene), poly(ethyl acrylate-butadiene), poly(propyl acrylate-butadiene), poly(butyl acrylate-butadiene), poly(styrene-isoprene), poly(methylstyrene-isoprene), poly(methyl methacrylate-isoprene), poly(ethyl methacrylate-isoprene), poly(propyl methacrylate-isoprene), poly(butyl methacrylate-isoprene), poly(methyl acrylate-isoprene), poly(ethyl acrylate-isoprene), poly(propyl acrylate-isoprene), poly(butyl acrylate-isoprene), polystyrene-propyl acrylate), poly(styrene-butyl acrylate), poly(styrene-butadiene-acrylic acid), poly(styrene-butadiene-methacrylic acid), poly(styrene-butadiene-acrylonitrile-acrylic acid); poly(styrene-butyl acrylate-acrylic acid), poly(styrene-butyl acrylate-methacrylic acid), poly(styrene-butyl acrylate-acrylonitrile), poly(styrene-butyl acrylate-acrylonitrile-acrylic acid), polystyrene-butadiene), poly(styrene-isoprene), poly(styrene-butyl methacrylate), poly(styrene-butyl acrylate-acrylic acid), poly(styrene-butyl methacrylate-acrylic acid), poly(butyl methacrylate-butyl acrylate), poly(butyl methacrylate-acrylic acid), poly(acrylonitrile-butyl acrylate-acrylic acid) and combinations thereof.

20. The article of claim 18, wherein the article is selected from the group consisting of a biochemical sensor, an optical detector, an antibacterial, a textile, a cosmetic, an electronic component, a fiber, and a cryogenic superconducting material.

* * * * *